(12) United States Patent
Isaacs et al.

(10) Patent No.: US 6,462,050 B1
(45) Date of Patent: Oct. 8, 2002

(54) THROMBIN INHIBITORS

(75) Inventors: Richard C. Isaacs; Kellie Cutrona; James C. Barrow, all of Harleysville; Harold G. Selnick, Ambler, all of PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/916,745

(22) Filed: Jul. 27, 2001

Related U.S. Application Data

(60) Provisional application No. 60/221,396, filed on Jul. 28, 2000.

(51) Int. Cl.$^7$ .................... A61K 31/497; C07D 401/12
(52) U.S. Cl. ................... 514/255.05; 544/405
(58) Field of Search ............... 544/405; 514/255.05

(56) References Cited

U.S. PATENT DOCUMENTS 6,011,038 A * 1/2000 Dorsey et al. ............... 514/252
6,147,078 A * 11/2000 Sanderson et al. .......... 514/252

\* cited by examiner

Primary Examiner—Emily Bernhardt
(74) Attorney, Agent, or Firm—Melvin Winokur; Valerie J. Camara; Richard S. Parr

(57) ABSTRACT

Compounds of the invention are useful in inhibiting thrombin and associated thrombotic occlusions having the following structure:

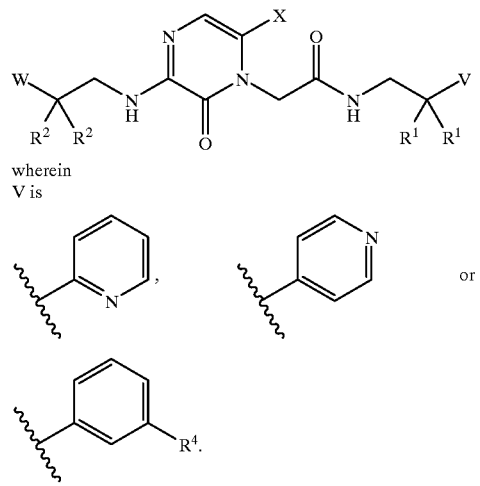

wherein V is

19 Claims, No Drawings

THROMBIN INHIBITORS

CROSS-REFERENCE TO RELATED APPLICATION

This application claims priority to provisional application No. 60/221,396, filed Jul. 28, 2000.

BACKGROUND OF THE INVENTION

Thrombin is a serine protease present in blood plasma in the form of a precursor, prothrombin. Thrombin plays a central role in the mechanism of blood coagulation by converting the solution plasma protein, fibrinogen, into insoluble fibrin.

Edwards et al., *J. Amer. Chem. Soc.*, (1992) vol. 114, pp. 1854–63, describes peptidyl a-ketobenzoxazoles which are reversible inhibitors of the serine proteases human leukocyte elastase and porcine pancreatic elastase.

European Publication 363 284 describes analogs of peptidase substrates in which the nitrogen atom of the scissile amide group of the substrate peptide has been replaced by hydrogen or a substituted carbonyl moiety.

Australian Publication 86245677 also describes peptidase inhibitors having an activated electrophilic ketone moiety such as fluoromethylene ketone or a-keto carboxyl derivatives.

R. J. Brown et al., *J. Med. Chem.*, Vol. 37, pages 1259–1261 (1994) describes orally active, non-peptidic inhibitors of human leukocyte elastase which contain trifluoromethylketone and pyridinone moieties.

H. Mack et al., *J. Enzyme Inhibition*, Vol. 9, pages 73–86 (1995) describes rigid amidino-phenylalanine thrombin inhibitors which contain a pyridinone moiety as a central core structure.

SUMMARY OF THE INVENTION

The invention includes a composition for inhibiting loss of blood platelets, inhibiting formation of blood platelet aggregates, inhibiting formation of fibrin, inhibiting thrombus formation, and inhibiting embolus formation in a mammal, comprising a compound of the invention in a pharmaceutically acceptable carrier. These compositions may optionally include anticoagulants, antiplatelet agents, and thrombolytic agents. The compositions can be added to blood, blood products, or mammalian organs in order to effect the desired inhibitions.

The invention also includes a composition for preventing or treating unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels, in a mammal, comprising a compound of the invention in a pharmaceutically acceptable carrier. These compositions may optionally include anticoagulants, antiplatelet agents, and thrombolytic agents.

The invention also includes a method for reducing the thrombogenicity of a surface in a mammal by attaching to the surface, either covalently or noncovalently, a compound of the invention.

DETAILED DESCRIPTION OF THE INVENTION AND PREFERRED EMBODIMENTS

Compounds of the invention are useful as thrombin inhibitors and have therapeutic value in for example, preventing coronary artery disease, and have the following structure:

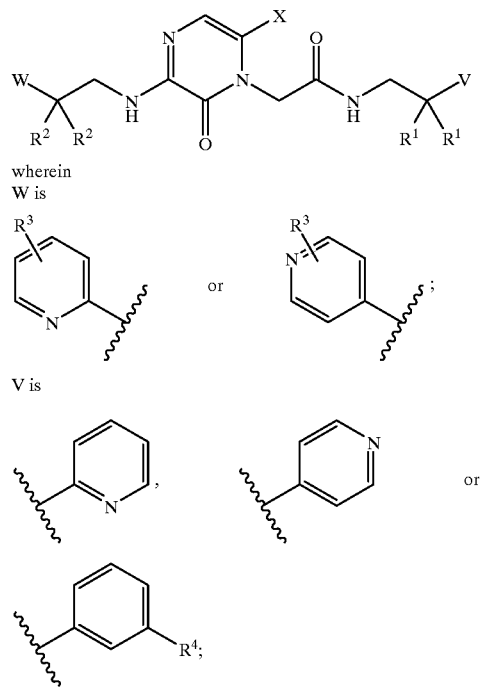

wherein
W is or

V is

, or

;

X is halogen, $C_{1-4}$alkyl, or cyano;

$R^1$ is hydrogen or halogen, provided that when $R^2$ is hydrogen, $R^1$ is halogen;

$R^2$ is hydrogen or halogen, provided that when $R^1$ is hydrogen, $R^2$ is halogen;

$R^3$ is hydrogen or $C_{1-4}$alkyl; and $R^4$ is hydrogen, halogen, or $C_{1-4}$ alkyl, and pharmaceutically acceptable salts thereof.

In a class of the compounds of the invention, X is Cl or $CH_3$.

In a group of this subclass, $R^1$ is hydrogen or F.

In a subgroup of this group, $R^2$ is hydrogen or F.

In a family of this subgroup, $R^3$ is hydrogen or $CH_3$. and $R^4$ is hydrogen or Cl.

Examples of this family are listed below. Inhibitory activity, as measured by the in vitro assay described in the specification, is represented by "*", indicating Ki greater than or equal to 20 nM, or "**" indicating Ki less than 20 nM.

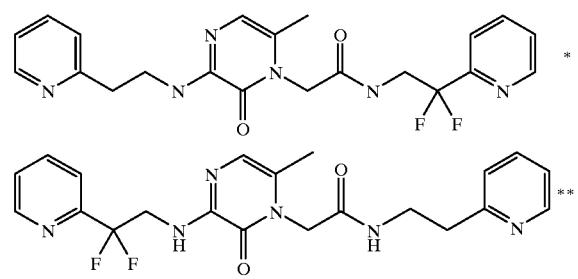

-continued

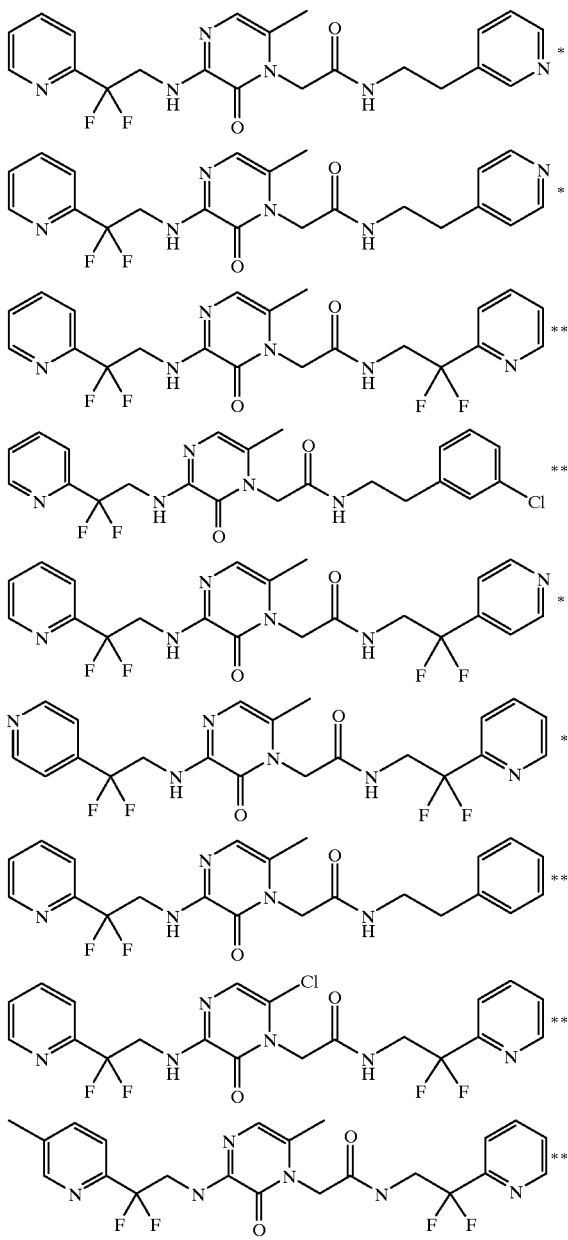

The compounds of the present invention may have chiral centers and occur as racemates, racemic mixtures and as individual diastereomers, or enantiomers with all isomeric forms being included in the present invention. The compounds of the present invention may also have polymorphic crystalline forms, with all polymorphic crystalline forms being included in the present invention.

When any variable occurs more than one time in any constituent or in formula I, its definition on each occurrence is independent of its definition at every other occurrence. Also, combinations of substituents and/or variables are permissible only if such combinations result in stable compounds.

Some abbreviations that may appear in this application are as follows:

| ABBREVIATIONS | |
|---|---|
| AcOH | acetic acid |
| CHCl$_3$ | chloroform |
| CH$_2$Cl$_2$ | dichloromethane |
| DCE | 1,2-dichloroethane |
| DMF | dimethylformamide |
| EDC | 1-ethyl-3-(3-dimethylaminopropyl) carbodiimide hydrochloride |
| Et$_2$O | diethyl ether |
| EtOAc | ethyl acetate |
| EtOH | ethanol |
| HCl | hydrochloric acid |
| HOBT | 1-hydroxybenzotriazole hydrate |
| KHSO$_4$ | potassium hydrogen sulfate |
| KOH | potassium hydroxide |
| LiOH | lithium hydroxide |
| MeOH | methanol |
| MgSO$_4$ | magnesium sulfate |
| NaBH$_4$ | sodium borohydride |
| NaHCO$_3$ | sodium hydrogen carbonate |
| NaN$_3$ | sodium azide |
| Na$_2$CO$_3$ | sodium carbonate |
| Na$_2$SO$_4$ | sodium sulfate |
| nBuLi | n-butyllithium |
| NCS | N-chlorosuccinimide |
| NH$_4$OH | ammonium hydroxide |
| NMM | N-methylmorpholine |
| Pd—C | palladium on activated carbon catalyst |
| PhCH$_3$ | toluene |
| TEA | triethylamine |
| TFA | trifluoroacetic acid |
| THF | tetrahydrofuran |
| TMSCN | trimethylsilyl cyanide |

As used herein except where noted, "alkyl" is intended to include both branched- and straight-chain saturated aliphatic hydrocarbon groups having the specified number of carbon atoms (Me is methyl, Et is ethyl, Pr is propyl, Bu is butyl). "Halogen", as used herein, means fluoro, chloro, bromo and iodo.

The pharmaceutically-acceptable salts of the compounds of Formula I (in the form of water- or oil-soluble or dispersible products) include the conventional non-toxic salts such as those derived from inorganic acids, e.g. hydrochloric, hydrobromoic, sulfuric, sulfamic, phosphoric, nitric and the like, or the quaternary ammonium salts which are formed, e.g., from inorganic or organic acids or bases. Examples of acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, nitrate, oxalate, pamoate, pectinate, persulfate, 3-phenylpropionate, picrate, pivalate, propionate, succinate, sulfate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

Thrombin Inhibitors—Therapeutic Uses—Method of Using

Anticoagulant therapy is indicated for the treatment and prevention of a variety of thrombotic conditions, particularly coronary artery and cerebrovascular disease. Those experienced in this field are readily aware of the circumstances requiring anticoagulant therapy. The term "patient" used herein is taken to mean mammals such as primates, including humans, sheep, horses, cattle, pigs, dogs, cats, rats, and mice.

Thrombin inhibition is useful not only in the anticoagulant therapy of individuals having thrombotic conditions, but is useful whenever inhibition of blood coagulation is required such as to prevent coagulation of stored whole blood and to prevent coagulation in other biological samples for testing or storage. Thus, the thrombin inhibitors can be added to or contacted with any medium containing or suspected of containing thrombin and in which it is desired that blood coagulation be inhibited, e.g., when contacting the mammal's blood with material selected from the group consisting of vascular grafts, stents, orthopedic prosthesis, cardiac prosthesis, and extracorporeal circulation systems.

Compounds of the invention are useful for treating or preventing venous thromboembolism (e.g. obstruction or occlusion of a vein by a detached thrombus; obstruction or occlusion of a lung artery by a detached thrombus), cardiogenic thromboembolism (e.g. obstruction or occlusion of the heart by a detached thrombus), arterial thrombosis (e.g. formation of a thrombus within an artery that may cause infarction of tissue supplied by the artery), atherosclerosis (e.g. arteriosclerosis characterized by irregularly distributed lipid deposits) in mammals, and for lowering the propensity of devices that come into contact with blood to clot blood.

Examples of venous thromboembolism which may be treated or prevented with compounds of the invention include obstruction of a vein, obstruction of a lung artery (pulmonary embolism), deep vein thrombosis, thrombosis associated with cancer and cancer chemotherapy, thrombosis inherited with thrombophilic diseases such as Protein C deficiency, Protein S deficiency, antithrombin III deficiency, and Factor V Leiden, and thrombosis resulting from acquired thrombophilic disorders such as systemic lupus erythematosus (inflammatory connective tissue disease). Also with regard to venous thromboembolism, compounds of the invention are useful for maintaining patency of indwelling catheters.

Examples of cardiogenic thromboembolism which may be treated or prevented with compounds of the invention include thromboembolic stroke (detached thrombus causing neurological affliction related to impaired cerebral blood supply), cardiogenic thromboembolism associated with atrial fibrillation (rapid, irregular twitching of upper heart chamber muscular fibrils), cardiogenic thromboembolism associated with prosthetic heart valves such as mechanical heart valves, and cardiogenic thromboembolism associated with heart disease.

Examples of arterial thrombosis include unstable angina (severe constrictive pain in chest of coronary origin), myocardial infarction (heart muscle cell death resulting from insufficient blood supply), ischemic heart disease (local anemia due to obstruction (such as by arterial narrowing) of blood supply), reocclusion during or after percutaneous transluminal coronary angioplasty, restenosis after percutaneous transluminal coronary angioplasty, occlusion of coronary artery bypass grafts, and occlusive cerebrovascular disease. Also with regard to arterial thrombosis, compounds of the invention are useful for maintaining patency in arteriovenous cannulas.

Examples of atherosclerosis include arteriosclerosis.

Examples of devices that come into contact with blood include vascular grafts, stents, orthopedic prosthesis, cardiac prosthesis, and extracorporeal circulation systems The thrombin inhibitors of the invention can be administered in such oral forms as tablets, capsules (each of which includes sustained release or timed release formulations), pills, powders, granules, elixers, tinctures, suspensions, syrups, and emulsions. Likewise, they may be administered in intravenous (bolus or infusion), intraperitoneal, subcutaneous, or intramuscular form, all using forms well known to those of ordinary skill in the pharmaceutical arts. An effective but non-toxic amount of the compound desired can be employed as an anti-aggregation agent. For treating ocular build up of fibrin, the compounds may be administered intraocularly or topically as well as orally or parenterally.

The thrombin inhibitors can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber or other polymers manufactured by the Dow-Corning Corporation.

The thrombin inhibitors can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The thrombin inhibitors may also be delivered by the use of monoclonal antibodies as individual carriers to which the compound molecules are coupled. The thrombin inhibitors may also be coupled with soluble polymers as targetable drug carriers. Such polymers can include polyvinlypyrrolidone, pyran copolymer, polyhydroxypropyl-methacrylamide-phenol, polyhydroxyethyl-aspartamide-phenol, or polyethyleneoxide-polylysine substituted with palmitoyl residues. Furthermore, the thrombin inhibitors may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

The dosage regimen utilizing the thrombin inhibitors is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the thrombin inhibitors, when used for the indicated effects, will range between about 0.01 mg per kg of body weight per day (mg/kg/day) to about 30 mg/kg/day, preferably 0.025–7.5 mg/kg/day, more preferably 0.1–2.5 mg/kg/day, and most preferably 0.1–0.5 mg/kg/day (unless specificed otherwise, amounts of active ingredients are on free base basis). For example, an 80 kg patient would receive between about 0.8 mg/day and 2.4 g/day, preferably 2–600 mg/day, more preferably 8–200 mg/day, and most preferably 8–40 mg/kg/day. A suitably prepared medicament for once a day administration would thus contain between 0.8 mg and 2.4 g, preferably between 2 mg and 600 mg, more preferably between 8 mg and 200 mg, and most preferably 8 mg and 40 mg, e.g., 8 mg, 10 mg, 20 mg and 40 mg. Advantageously, the thrombin inhibitors may be administered in divided doses of two, three, or four times daily. For administration twice a day, a suitably prepared medicament would contain between 0.4 mg and 4 g, preferably between 1 mg and 300 mg, more preferably between 4 mg and 100 mg, and most preferably 4 mg and 20 mg, e.g., 4 mg, 5 mg, 10 mg and 20 mg.

Intravenously, the patient would receive the active ingredient in quantities sufficient to deliver between 0.025–7.5 mg/kg/day, preferably 0.1–2.5 mg/kg/day, and more preferably 0.1–0.5 mg/kg/day. Such quantities may be administered in a number of suitable ways, e.g. large volumes of low concentrations of active ingredient during one extended period of time or several times a day, low volumes of high concentrations of active ingredient during a short period of time, e.g. once a day. Typically, a conventional intravenous formulation may be prepared which contains a concentration of active ingredient of between about 0.01–1.0 mg/ml, e.g. 0.1 mg/ml, 0.3 mg/ml, and 0.6 mg/ml, and administered in amounts per day of between 0.01 ml/kg patient weight and 10.0 ml/kg patient weight, e.g. 0.1 ml/kg, 0.2 ml/kg, 0.5 ml/kg. In one example, an 80 kg patient, receiving 8 ml twice a day of an intravenous formulation having a concentration of active ingredient of 0.5 mg/ml, receives 8 mg of active ingredient per day. Glucuronic acid, L-lactic acid, acetic acid, citric acid or any pharmaceutically acceptable acid/conjugate base with reasonable buffering capacity in the pH range acceptable for intravenous administration may be used as buffers. Consideration should be given to the solubility of the drug in choosing an The choice of appropriate buffer and pH of a formulation, depending on solubility of the drug to be administered, is readily made by a person having ordinary skill in the art.

The compounds can also be administered in intranasal form via topical use of suitable intranasal vehicles, or via transdermal routes, using those forms of transdermal skin patches well known to those of ordinary skill in that art. To be administered in the form of a transdermal delivery system, the dosage administration will, or course, be continuous rather than intermittent throughout the dosage regime.

The thrombin inhibitors are typically administered as active ingredients in admixture with suitable pharmaceutical diluents, excipients or carriers (collectively referred to herein as "carrier" materials) suitably selected with respect to the intended form of administration, that is, oral tablets, capsules, elixers, syrups and the like, and consistent with convention pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, distintegrating agents and coloring agents can also be incorporated into the mixture. Suitable binders include starch, gelatin, natural sugars such as glucose or beta-lactose, corn-sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch methyl cellulose, agar, bentonite, xanthan gum and the like.

The invention also includes a method for treating an inflammatory disease in a patient which comprises treating the patient with a composition comprising a compound of the present invention. Such diseases include but are not limited to nephritis, systemic lupus erythematosus, rheumatoid arthritis, glomerulonephritis, and sacoidosis.

The invention is also a method for treating an inflammatory disease in a patient that comprises treating the patient with a combination comprising a compound of the invention and an NSAID, e.g., a COX-2 inhibitor. Such diseases include but are not limited to nephritis, systemic lupus, erythematosus, rheumatoid arthritis, glomerulonephritis, vasculitis and sacoidosis.

The present invention is a method for relieving pain, fever and inflammation of a variety of conditions including nephritis, systemic lupus erythematosus, rheumatoid arthritis, glomerulonephritis, sacoidosis, rheumatic fever, symptoms associated with influenza or other viral infections, common cold, low back and neck pain, dysmenorrhea, headache, toothache, sprains and strains, myositis, neuralgia, synovitis, arthritis, including rheumatoid arthritis degenerative joint diseases (osteoarthritis), gout and ankylosing spondylitis, bursitis, burns, injuries, following surgical and dental procedures in a patient by administering to the patient a therapeutically effective amount of a compound of the invention. Thrombin inhibitors may also be useful for the treatment of dementia including pre-senile and senile dementia, and in particular, dementia associated with Alzheimer Disease.

In inflammatory diseases wherein fibrin formation is prominent, the fibrin may be a determinant of the pathology. Fibrin serves as a matrix onto which inflammatory cells can migrate and adhere. (see Sherman et al., 1977 *J. Exp. Med.* 145:76–85; Altieri et al., 1986 *J. Clin. Invest.* 78:968–976; Wright et al., 1983 *Proc. Natl. Acad. Sci.* 85:7734–7738; Altieri et al., 1993 *J. Biol. Chem.* 268;1847–1853). Fibrin also enhances expression of the inflammatory cytokine IL-lbeta and decreases expression of IL-I receptor antagonist by human peripheral blood mononuclear cells (see Perez 1995 *J. Immunol.* 154:1879–1887). The anticoagulants warfarin and heparin attenuate delayed-type hypersensitivity reactions and experimental nephritis in animals. (see Jasain et al., Immunopathogenesis of Rheumatoid Arthritis Eds. G. S. Panayi et al., Surrey, UK, Reedbooks, Ltd. and Halpern et al., 1965 *Nature* 205:257-259). Enzymatic defibrination with ancrod diminishes the degree of experimental nephritis (Naish et al., 1972 *Clin. Sci.* 42:643–646), systemic lupus erythematosus (Cole et al., 1990 *Kidney Int.* 37:29–35, and rheumatoid arthritis (see Busso et al., 1998 *J. Clin. Invest.* 102:41–50) in animals, and glomerulonephritis in man (see Kim For example, WUP coding region in another species may be isolated using induces arthritis in rabbits immunized with fibrin Dumonde et al., 1961 *British Journal of Experimental Pathology* XLIII:373–383), and antigen-induced arthritis in mice is exacerbated in urokinase-deficient mice wherein fibrinolysis synovial fibrin is compromised (see Busso et al., 1998 *J. Clin. Invest.* 102:41–50).

In diseases where fibrin deposition is prominent such as, but not limited to, rheumatoid arthritis, systemic lupus erythematosus, glomerulonephritis, vasculitis and sacoidosis, lowering the steady state concentration of fibrin by administration of a compound of the invention will, according to the instant invention, diminish the pathological inflammatory responses associated with these diseases.

Similarly, compounds of the invention will be useful as a partial or complete substitute for conventional NSAIDs in preparations wherein they are presently co-administered with other agents or ingredients. Thus in further aspects, the invention encompasses pharmaceutical compositions for treating inflammatory diseases as defined above comprising a non-toxic therapeutically effective amount of a compound of the invention as defined above and one or more ingredients such as another pain reliever including acetominophen or phenacetin; a potentiator including caffeine; an H2-antagonist, aluminum or magnesium hydroxide, simethicone, a decongestant including phenylephrine, phenylpropanolamine, pseudophedrine, oxymetazoline, ephinephrine, naphazoline, xylometazoline, propylhexedrine, or levo-desoxyephedrine; an antiitussive including codeine, hydrocodone, caramiphen, carbetapentane, or dextramethorphan; a diuretic; a sedating or non-sedating antihistamine. In addition the invention encompasses a method of treating inflammatory diseases comprising administration to a patient in need of such treatment a non-toxic therapeutically effect amount of a compound of the invention, optionally co-administered with one or more of such ingredients as listed immediately above.

The instant invention also involves a novel combination therapy comprising the administration of a therapeutically effective amount of an NSAID such as a COX-2 inhibitor in combination with a therapeutically effective amount of a compound of the invention to a mammal, and more particularly, to a human. The combination therapy is used to treat inflammatory diseases.

The instant pharmaceutical combinations comprising a compound of the invention in combination with an NSAID such as a COX-2 inhibitor include administration of a single pharmaceutical dosage formulation which contains both a compound of the invention and the NSAID, as well as administration of each active agent in its own separate pharmaceutical dosage formulation. Where separate dosage formulations are used, the compound of the invention and the NSAID can be administered at essentially the same time, i.e., concurrently, or at separately staggered times, i.e., sequentially. The "instant pharmaceutical combination" is understood to include all these regimens. Administration in these various ways are suitable for the present invention as long as the beneficial pharmaceutical effect of the compound of the invention and the NSAID are realized by the patient at substantially the same time. Such beneficial effect is preferably achieved when the target blood level concentrations of each active drug are maintained at substantially the same time. It is preferred that the compound of the invention and the NSAID be co-administered concurrently on a once-a-day dosing schedule; however, varying dosing schedules, such as the compound of the invention once per day and the NSAID once, twice or more times per day, or the NSAID once per day and the compound of the invention once, twice or more times per day, is also encompassed herein. A single oral dosage formulation comprised of both the compound of the invention and the NSAID is preferred. A single dosage formulation will provide convenience for the patient.

The instant invention also provides pharmaceutical compositions comprised of a therapeutically effective amount of an NSAID, or a pharmaceutically acceptable salt thereof, in combination with a therapeutically effective amount of a compound of the invention, or a pharmaceutically acceptable salt thereof, and a pharmaceutically acceptable carrier. One embodiment of the instant compositions is a single composition adapted for oral administration comprised of a therapeutically effective amount of a COX-2 inhibitor in combination with a therapeutically effective amount of a compound of the invention and a pharmaceutically acceptable carrier. The combination can also be administered in separate dosage forms, each having one of the active agents. If administered in separate dosage forms, the separate dosage forms are administered such that the beneficial effect of each active agent is realized by the patient at substantially the same time.

Common NSAIDs include salicylates such as aspirin, sodium salicylate, choline salicylate, salicylsalicylic acid, diflunisal, and salsalate; indoleacetic acids such as indomethacin and sulindac; pyrazoles such as phenylbutazone, oxyphenbutazone; pyrrolealkanoic acids such as tolmetin; phenylacetic acids such as ibuprofen, feroprofen, flurbiprofen, and ketoprofen; fenamates such as mefanamic acid, and meclofenamate; oxicams such as piroxicam; and naphthaleneacetic acids such as naproxen. Cyclo-oxygenase inhibitors such as COX-1 and COX-2 inhibitors are also NSAIDs.

Employing the human whole blood COX-1 assay and the human whole blood COX-2 assay described in C. Brideau et al, *Inflamm. Res.* 45: 68–74 (1996), herein incorporated by reference, preferably, the compounds have a cyclooxygenase-2 $IC_{50}$ of less than about 2 $\mu$M in the human whole blood COX-2 assay, yet have a cyclooxygenase-1 $IC_{50}$ of greater than about 5 $\mu$M in the human whole blood COX-1 assay. Also preferably, the compounds have a selectivity ratio of cyclooxygenase-2 inhibition over cyclooxygenase-1 inhibition of at least 10, and more preferably of at least 40. The resulting selectivity may indicate an ability to reduce the incidence of common NSAID-induced side effects.

The inhibitor of cyclooxygenase-2 may be administered at a dosage level up to conventional dosage levels for NSAIDs. Suitable dosage levels will depend upon the antiinflammatory effect of the chosen inhibitor of cyclooxygenase-2, but typically suitable levels will be about 0.001 to 50 mg/kg per day, preferably 0.005 to 30 mg/kg per day, and especially 0.05 to 10 mg/kg per day. The compound may be administered on a regimen of up to 6 times per day, preferably 1 to 4 times per day, and especially once per day.

The dosage regimen utilizing a compound of the invention in combination with the NSAID is selected in accordance with a variety of factors including type, species, age, weight, sex and medical condition of the patient; the severity of the condition to be treated; the route of administration; the renal and hepatic function of the patient; and the particular compound or salt or ester thereof employed. Since two different active agents are being used together in a combination therapy, the potency of each of the agents and the interactive effects achieved by combining them together must also be taken into account. A consideration of these factors is well within the purview of the ordinarily skilled clinician for the purpose of determining the therapeutically effective or prophylactically effective dosage amounts needed to prevent, counter, or arrest the progress of the condition.

Administration of the drug combination to the patient includes both self-administration and administration to the patient by another person.

Additional active agents may be used in combination with the compound of the invention in a single dosage formulation, or may be administered to the patient in a separate dosage formulation, which allows for concurrent or sequential administration. Examples of additional active agents which may be employed include HMG-CoA synthase inhibitors; squalene epoxidase inhibitors; squalene synthetase inhibitors (also known as squalene synthase inhibitors), acyl-coenzyme A: cholesterol acyltransferase (ACAT) inhibitors; probucol; niacin; fibrates such as clofibrate, fenofibrate, and gemfibrizol; cholesterol absorption inhibitors; bile acid sequestrants; LDL (low density lipoprotein) receptor inducers; vitamin B6 (also known as pyridoxine) and the pharmaceutically acceptable salts thereof such as the HCl salt; vitamin $B_{12}$ (also known as cyanocobalamin); β-adrenergic receptor blockers; folic acid or a pharmaceutically acceptable salt or ester thereof such as the sodium salt and the methylglucamine salt; and anti-oxidant vitamins such as vitamin C and E and beta carotene.

The thrombin inhibitors can also be co-administered with suitable anti-platelet agents, including, but not limited to, fibrinogen receptor antagonists (e.g. to treat or prevent unstable angina or to prevent reocclusion after angioplasty and restenosis), anticoagulants such as aspirin, thrombolytic agents such as plasminogen activators or streptokinase to achieve synergistic effects in the treatment of various vascular pathologies, or lipid lowering agents including anti-hypercholesterolemics (e.g. HMG CoA reductase inhibitors such as lovastatin and simvastatin, HMG CoA synthase inhibitors, etc.) to treat or prevent atherosclerosis. For example, patients suffering from coronary artery disease, and patients subjected to angioplasty procedures, would benefit from coadministration of fibrinogen receptor antagonists and thrombin inhibitors. Also, thrombin inhibitors enhance the efficiency of tissue plasminogen activator-mediated thrombolytic reperfusion. Thrombin inhibitors may be administered first following thrombus formation, and tissue plasminogen activator or other plasminogen activator is administered thereafter.

Typical doses of thrombin inhibitors of the invention in combination with other suitable anti-platelet agents, anticoagulation agents, or thrombolytic agents may be the same as those doses of thrombin inhibitors administered without coadministration of additional anti-platelet agents, anticoagulation agents, or thrombolytic agents, or may be substantially less that those doses of thrombin inhibitors administered without coadministration of additional anti-platelet agents, anticoagulation agents, or thrombolytic agents, depending on a patient's therapeutic needs.

The following examples and methods are illustrative of the invention as contemplated by the inventors and should not be construed as being limits on the scope or spirit of the instant invention. Unless otherwise stated, all NMR determinations were made using 400 MHz field strength.

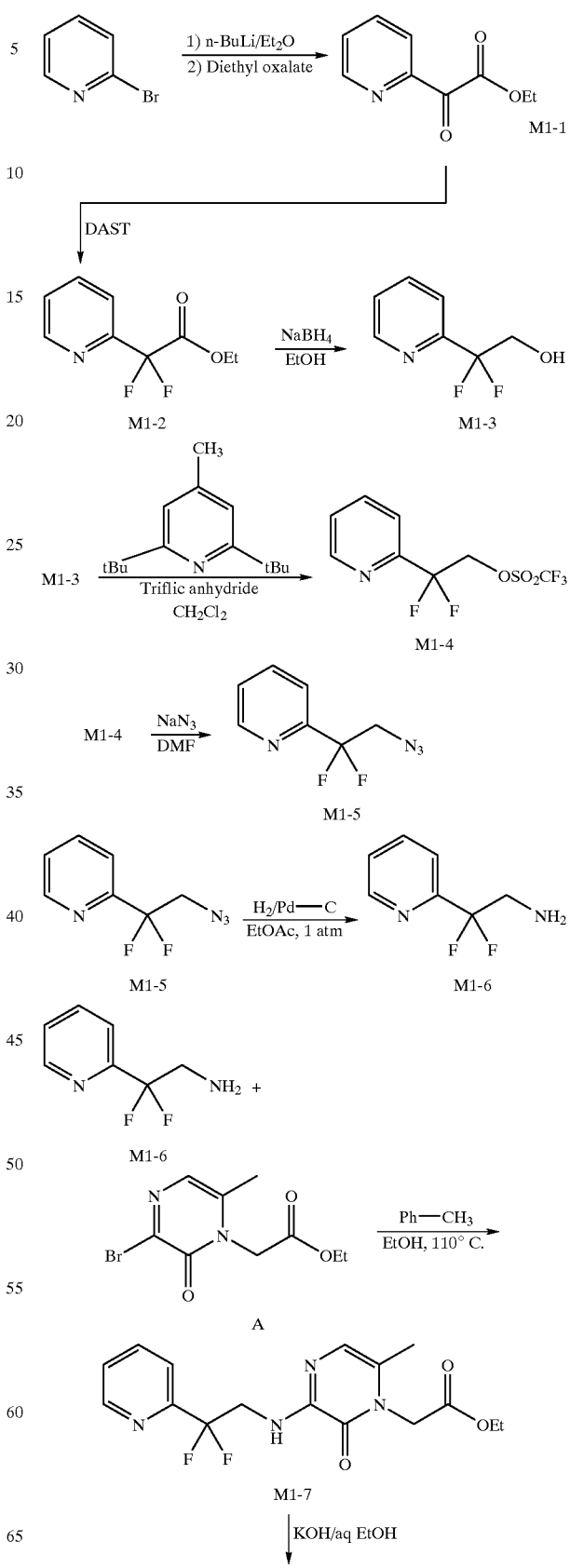

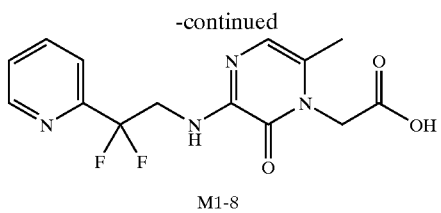

M1-8

The synthesis of the 2,2-difluoro-2-(2-pyridyl)ethylamine M1–6 involves generation of 2-lithiopyridine from 2-bromopyridine in ether, followed by reaction with diethyl oxalate to give the 2-pyridylketoester M-1. Treatment with excess diethylaminosulfurtrifluoride provides ethyl difluoro-2-pyridylacetate M1–2 which is reduced without purification using sodium borohydride. The resulting 2,2-difluoro-2-pyridylethanol M1–3 is purified by chromatography and converted to the corresponding triflate M1–4 using triflic anhydride and 2,6-di-t-butyl-4-methylpyridine as the base. The crude triflate is then treated with sodium azide in DMF to give 2,2-difluoro-2-(2-pyridyl)ethyl azide M1–5 which is also purified by silica gel chromatography. Reduction of the azide by catalytic hydrogenation provides the 2,2-difluoro-2-pyridylethylamine M1–6.

Condensation of this material with ethyl 3-bromo-6-methylpyrazin-2-one-1-acetate A in toluene/ethanol gives ethyl 3-(2,2-difluoro-2-(2-pyridyl)ethylamino)-6-methylpyrazin-2-one-1-acetate M1–7. Saponification provides the intermediate 3-(2,2-difluoro-2-(2-pyridyl)ethylamino)-6-methyl-pyrazin-2-one-1-acetic acid M1–8. The acid is then coupled with the appropriate amine.

METHOD 2

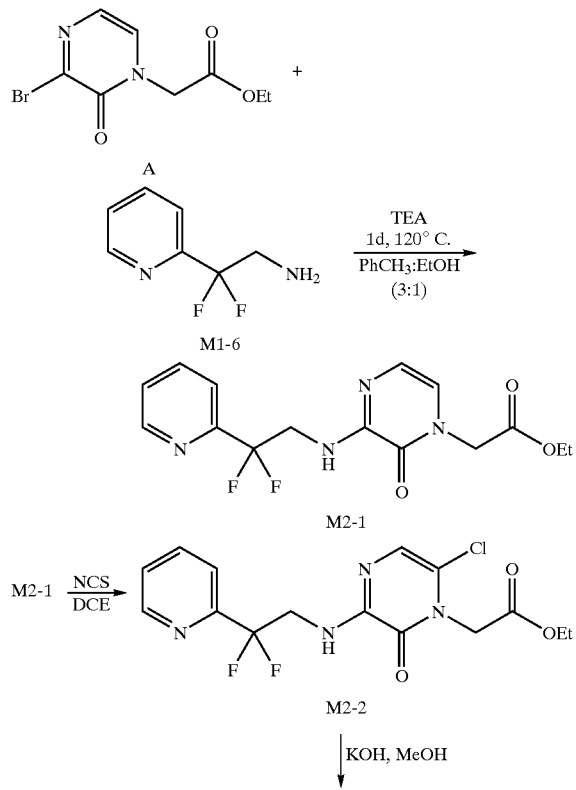

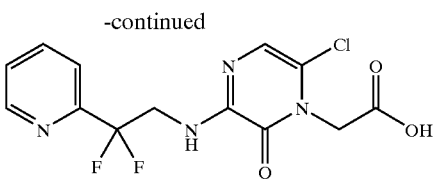

Ethyl 3-(2,2-difluoro-2-(2-pyridylethylamino) pyrazin(1H)-2-one-1-acetate (M2-1)

A solution of 4.80 g (30.4 mmol) of 2,2-difluoro-2-(2-pyridyl)ethylamine M1–6, 4.24 mL (30.4 mmol) of triethylamine and 7.93 g (30.4 mmol) of ethyl 3-bromopyrazin (1H)-2-one-1-acetate A was heated to 120° C. in a sealed tube overnight in 12 mL of toluene and 4 mL of ethanol. The reaction was concentrated and the residue was partitioned between dichloromethane and sat. aq. $NaHCO_3$. The aqueous layer was backwashed with 4 portions of dichloromethane. The combined organic layers were dried over $MgSO_4$ and the solvents removed at reduced pressure to give an oil that was chromatographed on $SiO_2$ using 60:40 to 40:60 hexane-EtOAc to give M2-1 as a yellow solid: $^1$H NMR (CDCl$_3$) δ8.67 (dd, 1H, 4.8, 0.7 Hz), 7.81 (ddd, 1H, 7.8, 7.8, 1.7 Hz), 7.69 (dd, 1H, 7.8, 1 Hz), 7.38 (dd, 1H1, 5.1, 7.0 Hz), 6.86 (d, 1H, 4.8 Hz), 6.54 (br t, 1H, 5.9 Hz), 6.40 (d, 1H, 4.6 Hz), 4.54 (s, 2H), 4.38 (td, 2H, 14.0, 6.4 Hz), 4.24 (q, 2H, 7.1 Hz), 1.29 (t, 3 H, 7.1 Hz).

Ethyl 3-(2,2-difluoro-2-(2-pyridylethylamino)-6-chloropyrazin(1H)-2-one-1-acetate (M2—2)

To a stirred solution of 6.81 g (20.1 mmol) of ethyl 3-(2,2-difluoro-2-(2-pyridylethylamino)pyrazin(1H)-2-one-1-acetate M2-1 and 2.42 g (18.1 mmol) of N-chlorosuccinimide in 100 mL of 1,2-dichloroethane was heated to reflux. An additional 242 mg (1.81 mmol) and 75 mg (0.56 mmol) of NCS were added to the reaction mixture after 1 h and 1.5 h, respectively. After 2.5 h total, the solution was cooled to room temperature and partitioned between dichloromethane (150 mL) and sat. aq. $NaHCO_3$ (200 mL). The layers were separated and the aqueous phase was backwashed with dichloromethane (2×200 mL). The combined organic layers were dried over $MgSO_4$ and the solution concentrated to a volume of 10 mL. This liquid was directly loaded onto a $SiO_2$ column and eluted with 65:35 to 55:45 hexane-EtOAc to give M2—2 as a yellow solid: $^1$H NMR (CDCl$_3$) δ8.68 (d, 1H, 4.8, Hz), 7.83 (ddd,1H, 7.7, 7.7, 1.6 Hz), 7.9 (dd, 1H, 7.9 Hz), 7.40 (dd, 1H, 4.9, 7.3 Hz), 6.96 (s, 1H), 6.49 (br t, 1H, 5.9 Hz), 4.89 (s, 2H), 4.38 (td, 2H, 13.9, 6.5 Hz), 4.26 (q, 2H, 7.1 Hz), 1.30 (t, 3 H, 7.1 Hz).

3-(2,2-Difluoro-2-(2-pyridylethylamino)-6-chloropyrazin(1H)-2-one-1-acetic acid (M2–3)

To a stirred solution of 7.27 g (19.5 mmol) of ethyl 3-(2,2-difluoro-2-(2-pyridylethylamino)-6-chloropyrazin (1H)-2-one-1-acetate M2—2 in 200 mL of methanol was added 39 mL (39.0 mmol) of 1M aq. potassium hydroxide. After 3 h the solution was acidified to pH=7 using conc. HCl, and concentrated at reduced pressure (azeotrope with PhCH$_3$) to give a white solid containing potassium chloride and M2–3: $^1$H NMR (CD$_3$OD) δ8.64 (d, 1H, 4.8 Hz), 7.93 (ddd,1H, 7.7, 7.7, 1.5 Hz), 7.70 (d, 1H, 8.0 Hz), 7.49 (dd, 1H, 5.2, 7.4 Hz), 6.80 (s, 1H), 4.67 (s, 2H), 4.27 (t, 2H, 13.9 Hz).

Preparation of Ethyl bromopyrazin(1H)-2-one-1-acetate (A)

The pyrazinone A is prepared by reacting ethylchlorooxalate 1 with ethyl glycinate 2 to afford 3 which is reacted with amine 4 to give compound 5. Compound 5 is cyclized with acid to give 6 which is reacted with phosphorous oxybromide to afford A.

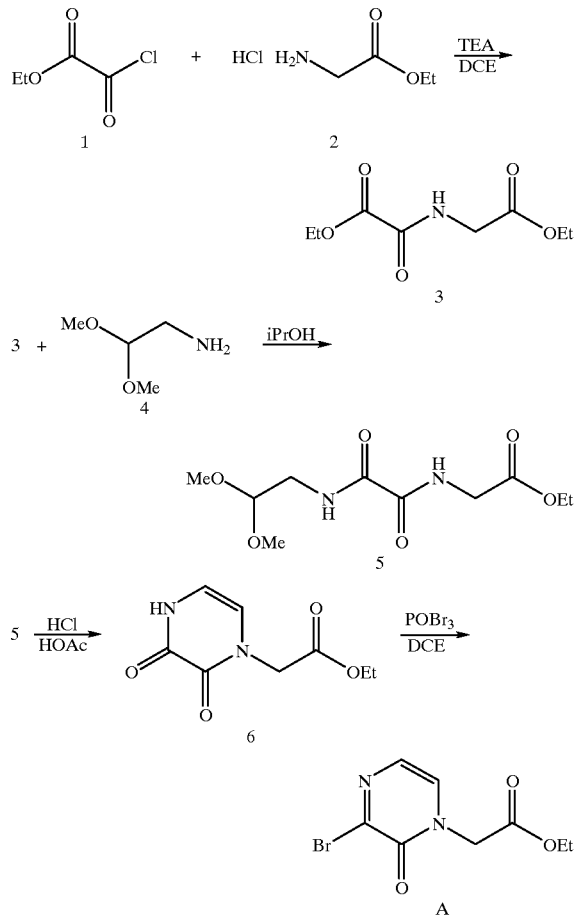

Ethyl N-(ethyl carboxymethyl)oxamate (3)

To a suspension of ethyl glycine·HCl 2 (38.4 g, 275 mmol) in 1,2-dichloroethane (360 mL) was added triethylamine (77.0 mL, 550 mmol) at room temperature. After stirring for 30 minutes the heterogenous mixture was cooled to 0° C. and ethyl oxalyl chloride 1 (30.3 mL, 275 mol) was added dropwise over the course of 1 h. Upon completion of the addition, the cooling bath was removed and the reaction was stirred at room temperature overnight. The reaction was diluted with water (250 mL) and the layers separated. The aqueous layer was backwashed with 2 portions of dichloromethane (250 mL). The combined organic layers were washed with water (250 mL), followed by brine (250 mL), dried over $MgSO_4$ and concentrated to give an oil 3 that was taken directly onto the next step.

N-(Ethyl carboxymethyl)-N'-(2,2-dimethoxyethyl) oxamide (5)

To a solution of the oxamate 3 (84.0 g, 414 mmol) in 2-propanol (500 mL) was added aminoacetaldehyde dimethyl acetal 4 (45.7 g, 435 mmol) in one portion. After stirring overnight at room temperature, the reaction mixture was concentrated to a thick orange oil. This thick slurry was diluted with 2-propanol (300 mL) and the solid was broken up with a spatula. Filtration afforded a solid which was further rinsed with an additional portion of 2-propanol. Removal of residual 2-propanol was accomplished via high vacuum to afford a light orange solid 5.: $^1$H NMR ($CDCl_3$) δ7.82 (br s, 1H), 7.50 (br s, 1H), 4.41 (t, 1H, 5.3 Hz), 4.24 (q, 2H, 2.71 Hz), 4.09 (d, 2H, 5.9 Hz), 3.47 (dd, 2H, 5.3, 6.2 Hz), 3.40 (s, 6H), 1.30 (t, 3H, 7.1 Hz).

Ethyl 3-hydroxypyrazin(1H)-2-one-1-acetate (6)

A solution of the oxamide 5 (89.8 g, 343 mmol), acetic acid (400 mL), and conc. HCl (2 mL) was heated to reflux. After 1 h the black reaction was concentrated to a thick oil (high vacuum employed to ensure complete removal of AcOH) which was diluted with EtOH (150 mL) and MeOH (150 ML). Scraping the thick black oil with a spatula induced precipitation of the product. The MeOH was removed via rotary evaporation and the remaining slurry was filtered and rinsed with EtOH (200 mL) to deliver a tan solid. Recrystallization from refluxing EtOH (300 mL) afforded an off-white powder 6: $^1$H NMR ($CD_3OD$) δ6.50 (d, 1H, 5.9 Hz), 6.36 (d, 1H, 5.9 Hz), 4.58 (s, 2H), 4.23 (q, 2H, 7.1 Hz), 1.28 (t, 3 H, 7.1 Hz). Further crude dione could be obtained upon concentration of the mother liquor.

Ethyl 3-bromopyrazin(1H)-2-one-1-acetate (A)

A solution of the hydroxypyrazinone 6 (25.0 g, 126 mmol) and phosphorous oxybromide (37.9 g, 132 mmol) in 1,2-dichloroethane (250 mL) was heated to reflux. After 8 h the reaction mixture was treated with sat. aq. $Na_2CO_3$ (250 mL) and stirred for 1 h. The mixture was diluted with water (100 mL) and dichloromethane (100 mL), the layers were separated and the aqueous layer was backwashed with EtOAc (3×200mL). The combined organics were dried ($MgSO_4$), and concentrated to give an oil which was stored on a high vacuum line overnite to afford brown solid A: $^1$H NMR ($CDCl_3$) δ7.17 (d, 1H, 4.2 Hz), 7.07 (d, 1H, 4.2 Hz), 4.65 (s, 2H), 4.27 (q, 2H, 7.2 Hz), 1.31 (t, 3 H, 7.2 Hz).

The following examples are illustrative of the invention as contemplated by the inventors and should not be construed as being limits on the scope or spirit of the instant invention.

EXAMPLE 1

Preparation of N-(2,2-Difluoro-2-pyridin-2-yl-ethyl)-2-(6-methyl-2-oxo-3-phenethylamino-2H-pyrazin-1-yl)-acetamide

This compound was prepared following Method 2. The Example describes exemplary synthetic techniques and conditions which are useful for preparing compounds of the invention.

Step A: N-(1-Cyanoethyl)glycine benzyl ester hydrochloride (1—1)

TMSCN (4.27 ml, 32 mmol) was added cautiously (reaction is exothermic) to a stirred solution of glycine benzyl ester (5.3 g, 32 mmol, prepared from the HCl salt by partitioning between EtOAc and $NaHCO_3$ solution) and acetaldehyde (1.8 ml, 32 mmol) in methylene chloride (11 ml). After 4 h the volatiles were removed in vacuo and the residue was taken up in EtOAc and was washed with brine, dried (Na$_2$SO$_4$) and evaporated in vacuo to an oil. The oil was redissolved in EtOAc and 9.9 M HCl in EtOH (38.4 mmol) was added to give a crystalline precipitate which was isolated by filtration and washing with EtOAc, to give 1–11: $^1$H NMR (CDCl$_3$) δ1.49 (d, J=7.1 Hz, 3 H, CH$_3$), 3.54 (d, J=17.3 Hz, 1 H, CH$_A$H$_B$), 3.64 (d, J=17.3 Hz, 1 H, CH$_A$H$_B$), 3.74 (q, J=7.0 Hz, 1 H, a-CH), 5.18 (s, 2 H, CH$_2$O), 7.36 (s, 5 H, Ph).

Step B: (3,5-Dichloro-6-methyl-2-oxo-2H-pyrazin-1-yl) acetic acid benzyl ester (1–2)

A stirred mixture of oxalyl chloride (9.3 ml, 107 mmol) and N-(1-cyanoethyl)glycine benzyl ester hydrochloride (6.8 g, 26.7 mmol) in 1,2-dichlorobenzene (25 ml) was heated to 100° C. for 15 h. The excess reagent was evaporated in vacuo and the residue was purified by flash chromatography (eluting first with hexanes to remove the dichlorobenzene, then with 3:2 hexanes/ethyl acetate) to give a solid which was triturated with 1:1 hexanes/ethyl acetate to give 1 -2 as a pale green crystalline solid: $^1$H NMR (CDCl$_3$) δ2.35 (s, 3 H, CH$_3$), 4.88 (s, 2 H, CH$_2$), 5.24 (s, 2 H, CH$_2$), 7.38 (m, 5 H, Ph).

Step C: (5-Chloro-6-methyl-2-oxo-3-phenethylamino-2H-pyrazin-1-yl)acetic acid benzyl ester (1–3)

2-Phenethylamine (0.38 ml, 3.0 mmol) was added to a stirred mixture of (3,5-dichloro-6-methyl-2-oxo-2H-pyrazin-1-yl)acetic acid benzyl ester (327 mg, 1.00 mmol) in EtOAc (2 ml) and the resulting mixture was heated to reflux under argon. After 2 h the reaction was cooled, diluted with EtOAc (the product is sparingly soluble), washed with 10% citric acid solution and brine, dried (Na$_2$SO$_4$) and evaporated in vacuo to give 1–3 as a crystalline solid. $^1$H NMR (CDCl$_3$) δ2.21 (s, 3 H, CH$_3$), 2.93 (t, J=7.1 Hz, 2 H, PhCH$_2$), 3.67 (q, J=7.1 Hz, 2 H, CH$_2$NH), 4.79 (s, 2 H, CH$_2$), 5.21 (s, 2 H, CH$_2$), 6.10 (br t, 1 H), 7.20–7.39 (m, 10 H, 2 Ph).

Step D: (5-Chloro-6-methyl-2-oxo-3-phenethylamino-2H-pyrazin-1-yl)acetic acid (1–4)

Water (1 ml) was added to a stirred solution of (5-chloro-6-methyl-2-oxo-3-phenethylamino-2H-pyrazin-1-yl)acetic acid benzyl ester (436 mg) in 1:1 THF/MeOH (6 ml) and LiOH.H$_2$O was added to the resulting mixture. After 2 h, the reaction mixture was diluted with water and washed with EtOAc. The aqueous layer was acidified with 10% KHSO4 solution to give a cloudy mixture that was extracted with methylene chloride. The organic layer was dried (Na$_2$SO$_4$) and evaporated in vacuo to give 1–4 as a crystalline solid. $^1$H NMR (DMSO-d$_6$) δ2.19 (s, 3 H, Me), 2.84 (t, J=7.0 Hz, 2 H, PhCH$_2$), 3.45 (q, J=7.0 Hz, 2 H, CH$_2$NH), 4.70 (s, 2 H, CH$_2$CO$_2$), 7.18–7.31 (m, 5 H, Ph), 7.46 (br s, 1H, NH).

Step E: (6-Methyl-2-oxo-3-phenethylamino-2H-pyrazin-1-yl)acetic acid (1–5)

(5-Chloro-6-methyl-2-oxo-3-phenethylamino-2H-pyrazin-1-yl)acetic acid (13.4 g, 41.6 mmol) was added to a stirred solution of potassium hydroxide (7.28 g, 110 mmol, assuming 15% water in the pellets) in water (600 ml). After degassing the resulting solution with argon, 10% Pd/C (6.3 g) was added and the mixture then stirred under a balloon of hydrogen. After 16 h, HPLC analysis showed that 1% of the starting material remained. The mixture was filtered through Celite and the filtrate was adjusted to pH 2 with 3N KHSO$_4$ solution. The resulting precipitate was collected by filtration and washed with water. Drying for 16 h at 0.5 mm Hg gave 1–5 as a crystalline solid: $^1$H NMR (DMSO-d$_6$) δ2.11 (s, 3 H, Me), 2.87 (t, J=7.6 Hz, 2 H, PhCH$_2$), 3.53 (br s, 2 H, CH$_2$NH), 4.68 (s, 2 H, CH$_2$CO$_2$), 6.68 (s, 1 H, pyrazinone H-5), 7.20–7.31 (m, 5 H, Ph), 8.16 (br s, 1 H, NH).

Step F: Ethyl difluoro-2-pyridyl acetate (1–6)

Ethyl bromodifluoroacetate (11.4 ml, 89 mmol) was added slowly to a suspension of zinc dust (100 mesh, 4.9 g, 75 mmol) in THF (90 ml) at 0° C. With the reaction mixture vented, the cold bath was removed and the reaction mixture allowed to warm gradually to room temperature. An exothermic reaction ensued and all the zinc was consumed within 1 h.

Simultaneously, in a separate reaction flask, dimethylcarbamoyl chloride (4.97 ml, 54 mmol) was added at room temperature to a solution of pyridine-N-oxide (5.13 g, 54 mmol) in THF (60 ml). A thick white precipitate resulted. After stirring for 1 h, to this mixture was then added the Reformatsky reagent as prepared above. The resulting reaction mixture was stirred at room temperature overnight. The solvent was removed under reduced pressure and the residue diluted with ethyl acetate and washed with water. The aqueous extracts were extracted with ether and the combined organics dried over sodium sulfate. Filtration and removal of the solvents left an oil which was carefully purified by flash chromatography(5: 1 to 4:1 hexane/EtOAc). The less polar isomer is ethyl difluoro-2-pyridyl acetate 1–6: $^1$H NMR (CDCl$_3$) δ8.65 (d, J=4.8 Hz, 1 H), 7.86 (m, 1 H), 7.74 (dd, J=0.9, 7.9 Hz, 1 H), 7.41–7.44 (m, 1 H), 4.38 (q, J=7.1 Hz, 2 H) 1.33 (t, J=7.1 Hz, 3 H). The more polar isomer is ethyl difluoro-4-pyridyl acetate: $^1$H NMR (CDCl$_3$) δ8.75 (m, 2 H), 7.51 (m, 2 H), 4.31 (q, J=7.1 Hz, 2 H) 1.30 (t, J=7.1 Hz, 3 H).

Step G: 2,2-Difluoro-2-(2-pyridyl)ethanol (1–7)

Sodium borohydride (376 mg, 9.9 mmol) was added to a solution of ethyl difluoro-2-pyridyl acetate (2 g, 9.9 mmol) in ethanol (100 ml) at 0° C. After stirring for 0.25 h, the cold bath was removed, and stirring continued another 1 h. The solvent was then removed under reduced pressure and the residue was partitioned between EtOAC and water. The organic phase was washed with saturated aqueous sodium bicarbonate. The organic phase was extracted with dichloromethane and the extracts then washed with sodium bicarbonate. The combined organic layers were dried over Na$_2$SO$_4$ and the solvents removed to give 1–7 as an almost colorless solid: $^1$H NMR (CDCl$_3$) δ8.61 (d, 1H, 4.5 Hz), 7.88 (td,1H, 8.0, 1.7 Hz), 7.73 (d, 1H, 7.8 Hz), 7.4–7.45 (m, 1H), 4.25 (td,2 H, 12.5, 7.1 Hz), 3.46 (t, 1H, 6.6 Hz).

Step H: 2,2-Difluoro-2-(2-pyridyl)ethyl trifluoromethanesulfonate (1–8)

To a stirred -78° C. solution of 50 mg (0.31 mmol) of 2,2-difluoro-2-(2-pyridyl)ethanol and 100 mg (0.49 mmol) of 2,6-di-t-butyl-4-methylpyridine in 1.0 ml of CH$_2$Cl$_2$ was added dropwise 79 μL (0.47 mmol) of trifluoromethansulfonic anhydride. After the addition, the cold bath was removed, and stirring continued for 0.5 h. The reaction was diluted with 2 ml of pentane, and the resulting precipitate washed with pentane. The filtrate was evaporated in vacuo to dryness to give 1–8 as a yellow solid: $^1$H NMR (CDCl$_3$) δ8.66 (d, 1H, 4.9 Hz), 7.89 (td,1H, 7.7, 1.7 Hz), 7.76 (d, 1H, 7.9 Hz), 7.45–7.49 (m, 1H), 5.12 (t, 2 H, 11.9 Hz).

Step I: 2,2-Difluoro-2-(2-pyridyl)ethyl azide (1–9)

A solution of 105 mg (0.31 mmol) of 2,2-difluoro-2-(2-pyridyl)ethyl trifluoromethanesulfonate and 43 mg (0.66 mmol) of sodium azide in 1.0 ml of DMF was heated at 60° C. After 1.5 h, the mixture was cooled, diluted with water and extracted with two portions of ether. The combined organic layers were washed twice with water, brine and dried over MgSO$_4$. The solvents were removed at reduced pressure to give 1–9 as a brown oil: 1H NMR (CDCl$_3$) δ8.68 (d, 1H, 4.2 Hz), 7.86 (td,1H, 7.8, 1.5 Hz), 7.72 (d, 1H, 7.8 Hz), 7.40–7.45 (m, 1H), 4.03 (t, 2 H, 13.2 Hz).

Step J: 2,2-Difluoro-2-(2-pyridyl)ethylamine (1–10)

A stirred solution of 100 mg of 2,2-difluoro-2-(2-pyridyl)ethyl azide was hydrogenated in 10 ml of ethyl acetate over 100 mg of 10% palladium on carbon under a balloon of hydrogen for 1 h. The catalyst was removed by filtration and the solvents removed at reduced pressure to give 1–10 as a yellow oil: $^1$H NMR (CDCl$_3$) δ6 8.66 (d, 1H, 4.2 Hz), 7.82 (td,1H, 7.7, 1.7 Hz), 7.68 (d, 1H, 8.1 Hz), 7.37–7.40 (m, 1H), 3.44 (t, 2 H, 14.3 Hz), 1.41 (br s, 2H).

Step K: N-(2,2-Difluoro-2-pyridin-2-yl-ethyl)-2-(6-methyl-2-oxo-3-phenethylamino-2H-pyrazin-1-yl)acetamide (1–11)

To a solution of 3-(2-phenethylamino)-6-methyl-1-methylene-carboxypyrazinone (217 mg, 0.76 mmol), 2,2-difluoro-2-(2-pyridyl)ethyl-amine (100 mg 0.63 mmol), EDC (145 mg, 0.76 mmol) and HOBT (102 mg, 0.75 mmol) in DMF (5 ml) was added N-methylmorpholine (0.7 ml, 6.3 mmol). After stirring at room temperature overnight, the solvent was removed in vacuo and water added to the resulting residue. 1–11 precipitated as a white solid which was collected, washed well with water and dried. Mass Spectrum: Found: (M+1) 428.3.

EXAMPLE 2

Preparation of N-(2,2-Difluoro-2-pyridin-2-ylethyl)-2-[6-methyl-2-oxo-3-(2-pyridin-2-yl)amino-2H-pyrazin-1-yl] acetamide

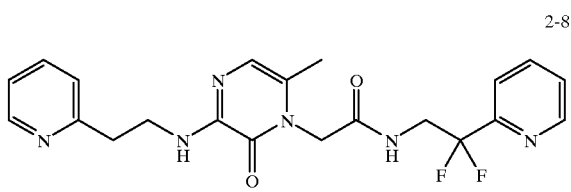

2-8

Step A: N-Ethoxycarbonylmethyl-oxalamic acid ethyl ester (2-1)

Triethylamine (12.5 ml, 90 mmol) was added to a suspension of ethyl glycine·HCl (5.6 g, 40 mmol ) in 1,2-dichloroethane (10 ml) at room temperature. After stirring for 30 minutes the heterogenous mixture was cooled to 0° C. Ethyl oxalyl chloride (5.3 ml, 47 mmol) was then added in a dropwise manner. Upon completion of the addition, the reaction mixture was allowed to warm gradually to room temperature and stirred there for 5 h. The reaction mixture was then washed with a dilute brine solution. The aqueous phase was saturated with NaCl and then extracted with a 1:1 mixture of ether and ethyl acetate. The combined organic phases were then washed once with brine and dried over sodium sulfate. Concentration gave 2-1 as an orange oil.

Step B: [(2-Hydroxy-1-propylaminooxalyl)-amino]-acetic acid ethyl ester (2—2)

To a stirred solution of N-ethoxycarbonylmethyl-oxalamic acid ethyl ester (6.13 g, 30.2 mmol) in absolute ethanol (30 ml) was added 1-amino-2-propanol (2.33 ml, 30.2 mmol) in one portion. The reaction mixture solidified over a period of stirring under argon for 2 h. The reaction mixture was dissolved in chloroform (50 ml) and then rotavaped to dryness. This was repeated with 100 ml of CHCl$_3$ and then the product was dried under in vacuo to give 2—2 as a colorless solid: $^1$H NMR (CDCl$_3$) δ7.88 (br s, 1H), 7.77 (br s, 1H), 4.24 (q, 2H, 7.1 Hz), 4.09 (d, 2H, 5.9 Hz), 3.98 (br s, 1H), 3.55–3.45 (m, 1H), 3.25-3.17 (m, 1H), 2.13 (br s, 1H), 1.30 (t, 3H, 7.1 Hz), 1.23 (d, 3H, 6.3 Hz).

Step C: [(2-Oxo-1-propylaminooxalyl)-amino]-acetic acid ethyl ester (2–3)

To a stirred slurry of of [(2-hydroxy-1-propylaminooxalyl)-amino]-acetic acid ethyl ester (3.98 g, 17.1 mmol) in H20 (24 ml) under argon at 50° C. was added ruthenium (III) chloride hydrate (36 mg, 0.17 mmol). The flask was removed from the heating bath, and a solution of sodium bromate (2.59 g, 17.1 mmol) in H$_2$O (24 ml) was added dropwise so that the temperature of the reaction stayed below 60° C. The reaction mixture was allowed to cool to room temperature, and then diluted with EtOAc and brine. The aqueous layer was extracted with two portions of EtOAc, and then saturated with solid NaCl and extracted again. The combined organic layers were washed with brine, dried over Na$_2$SO$_4$ and treated with activated carbon. Evaporation of the solvents and drying at reduced pressure gave 2–3 as a colorless solid: $^1$H NMR (CDCl$_3$) δ7.88 (br s, 1H), 7.80 (br s, 1H), 4.24 (q, 2H, 7.1 Hz), 4.20 (d, 2H, 5.1 Hz), 4.09 (d, 2H, 5.7 Hz), 2.23 (s, 3H), 1.35–1.25 (m, 3H), Step D: Ethyl (3-hydroxy-6-methyl-2-oxo-2H-pyrazin-1-yl)-acetate (2–4)

A solution of [(2-oxo-1-propylaminooxalyl)-amino]-acetic acid ethyl ester (3.43 g, 14.9 mmol), TFA (1.15 ml, 14.9 mmol) and trifluoroacetic anhydride (2.10 ml, 14.9 mmol) in acetic acid (60 ml) was heated at 80° C. under argon for 7h. After HPLC analysis of the reaction progress, additional TFA (766 μL, 9.9 mmol) and trifluoroacetic anhydride (1.4 ml, 9.9 mmol) were added and the reaction mixture was then heated for an additional 24 h. The reaction mixture was then cooled to room temperature following which, the solvents were removed under reduced pressure. Acetic acid (7 ml) was added to the residue and the resulting mixture heated at 60° C. for 10 min. Isopropyl acetate (iPAc) (35 ml) was added dropwise to the warm mixture. After the addition, the slurry was allowed to cool to room temperature, filtered, and washed with 1:5 HOAc-iPAc. The resulting solid was air dried to give 2-4 as an almost colorless solid: $^1$H NMR (CDCl$_3$) δ10.92 (br s, 1H), 6.185 (s, 1H), 4.66 (s, 2H), 4.25 (q, 2H, 7.1 Hz), 2.08 (s, 3H), 1.30 (t, 3H, 7.1 Hz).

Step E: Ethyl (3-bromo-6-methyl-2-oxo-2H-pyrazin-1-yl)-acetate (2–5)

A stirred slurry of 505 mg (2.38 mmol) of 1-(ethoxycarbonyl-methyl)-3-hydroxy-6-methylpyrazinone and 756 mg (2.64 mmol) of phosphorous oxybromide in 1.7 ml of CHCl$_3$ was stirred at 50° C. under a slow stream of Ar for 1.5 h, then allowed to cool to rt overnight. The reaction mixture was diluted with CHCl$_3$ and ice water, basified with NH$_4$OH, and extracted with CHCl$_3$. The combined organic layers were dried over Na$_2$SO$_4$, treated with activated carbon, filtered and concentrated to give 2–5 as an orange colored solid: $^1$H NMR (CDCl$_3$) δ7.06 (s, 1H), 4.77 (s, 2H), 4.27 (q, 2H, 7.2 Hz), 2.24 (s, 3H), 1.31 (t, 3H, 7.2 Hz).

Step F: Ethyl [3-(2-Pyridin-2-yl-ethylamino)-6-methyl-2-oxo-2H-pyrazin-1-yl]-acetate (2–6)

A solution of 7.13 g (45.1 mmol) of 2-(2-aminoethyl)-pyridine and 12.4 g (45.1 mmol) of ethyl 3-bromo-6-methylpyrazin(1H)-2-one-1-acetate was heated to 125° C. in a sealed tube overnight in 15 ml of toluene and 15 ml of ethanol. The reaction was concentrated and the residue was diluted with ethyl acetate, washed with 15% NaHCO$_3$ and the aqueous layer backwashed with 3 portions of ethyl acetate. The combined organic layers were dried over MgSO$_4$ and the solvents removed at reduced pressure to give an oil that was chromatographed on SiO$_2$ using 50:50 hexane-EtOAc to give 2–6 as a pale yellow solid.

Step G: [3-(2-Pyridin-2-yl-ethylamino)-6-methyl-2-oxo-2H-pyrazin-1-yl]-acetic acid (2–7)

To a stirred solution of 9.67 g (27.5 mmol) of ethyl 3-(2-pyridin-2-ylethylamino)-6-methylpyrazin(1H)-2-one- 1-acetate in 100 ml of methanol was added 8.58 g (153.0 mmol) of potassium hydroxide in 20 ml of water. After 1 h, the solution was concentrated at reduced pressure, and the residue dissolved in 25 ml of water. This solution was acidified to pH=7 using 1.3 M HCl, and concentrated at reduced pressure to give a yellow solid containing potassium chloride and 2–7.

Step H: N-(2,2-Difluoro-2-pyridin-2-ylethyl)-2-[6-methyl-2-oxo-3-(2-pyridin-2-yl)amino-2H-pyrazin-1-yl]acetamide (2–8)

2–8 was prepared from [3-(2-Pyridin-2-yl-ethylamino)-6-methyl-2-oxo-2H-pyrazin-1-yl]-acetic acid and 2,2-difluoro-2-(2-pyridyl)ethylamine essentially according to the procedure of Example 1, Step K. Mass Spectrum: Found: (M+1) 429.3.

EXAMPLE 3

Preparation of 2-[3-(2,2-Difluoro-2-pyridin-2-yl-ethylamino)-6-methyl-2-oxo-2H-pyrazin-1-yl]-N-(2-pyridin-3-ylethyl)-acetamide

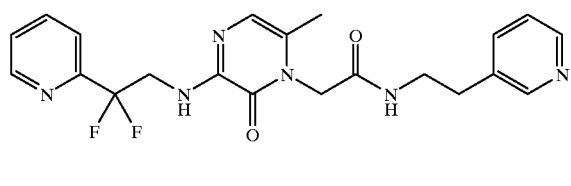

3-1

3-1 was prepared from [3-(2,2-difluoro-2-pyridin-2-yl-ethylamino)-6-methyl-2-oxo-2H-pyrazin-1-yl]-acetic acid and 3-(2-aminoethyl)pyridine essentially according to the procedure of Example 1, Step K. It was characterized as the hydrochloride salt. Mass Spectrum: Found: (M+1) 429.2.

EXAMPLE 4

Preparation of 2-[3-(2,2-Difluoro-2-pyridin-2-yl-ethylamino)-6-methyl-2-oxo-2H-pyrazin-1-yl]-N-(2-pyridin-4-ylethyl)-acetamide

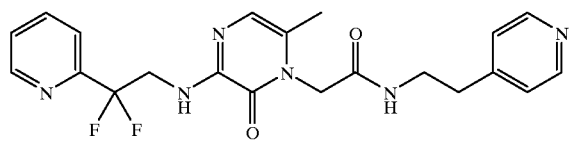

4-1

4-1 was prepared from [3-(2,2-difluoro-2-pyridin-2-yl-ethylamino)-6-methyl-2-oxo-2H-pyrazin-1-yl]-acetic acid and 4-(2-aminoethyl)pyridine essentially according to the procedure of Example 1, Step K. It was characterized as the hydrochloride salt. Mass Spectrum: Found: (M+1) 429.2.

EXAMPLE 5

Preparation of N-(2,2-Difluoro-2-pyridin-2-yl-ethyl)-2-[3-(2,2-difluoro-2-pyridin-2-yl-ethylamino)-6-methyl-2-oxo-2H-pyrazin-1-yl]-acetamide

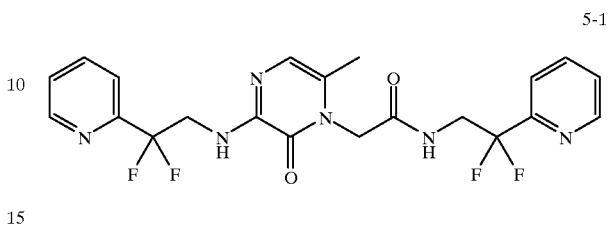

5-1

5-1 was prepared from [3-(2,2-difluoro-2-pyridin-2-yl-ethylamino)-6-methyl-2-oxo-2H-pyrazin-1-yl]-acetic acid and 2,2-difluoro-2-(2-pyridyl)ethyl amine essentially according to the procedure of Example 1, Step K. Mass Spectrum: Found: (M+1)465.2.

EXAMPLE 6

Preparation of N-(2,2-Difluoro-2-pyridin-2-yl-ethyl)-2-[3-(2,2-difluoro-2-pyridin-4-yl-ethylamino)-6-methyl-2-oxo-2H-pyrazin-1-yl]-acetamide

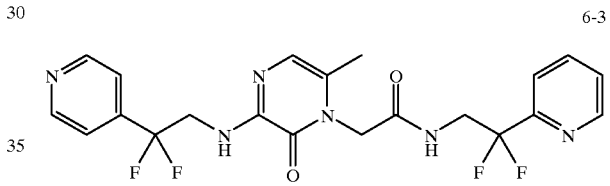

6-3

Step A: 2,2-Difluoro-2-(4-pyridyl)ethylamine (6–1)

6-1 was prepared from ethyl difluoro4-pyridyl acetate (see Example 1, Step F) essentially according to the procedures outlined for Example 1, Steps G through J. $^1$H NMR (CDCl$_3$) δ8.73 (d, 2H, 4.8 Hz), 7.39 (d, 2H, 4.6 Hz), 3.18 (t, 2H, 14.5 Hz), 1.41 (br s, 2H).

Step B: [3-(2,2-Difluoro-2-pyridin-4-ylethylamino)-6-methyl-2-oxo-2H-pyrazin-1-yl]-acetic acid (6-2)

6-2 was prepared essentially according to the procedure of Example 2, Steps F and G by substituting 2,2-difluoro-2-(4-pyridyl)ethylamine for 2,2-difluoro-2 -(2-pyridyl) ethylamine in Step F. $^1$H NMR (CD$_3$OD) δ8.62 (d, 2H, 5.7 Hz), 6.56 (s, 1H), 4.75 (s, 2H), 4.13 (t, 2H, 13.7 Hz), 2.12 (s, 3H).

Step C: N-(2,2-Difluoro-2-pyridin-2-yl-ethyl)-2-[3-(2,2-difluoro-2-pyridin-4-yl-ethylamino)-6-methyl-2H-pyrazin-1-yl]-acetamide (6-3) 6-3 was prepared from [3-(2,2-difluoro-2-pyridin-4-ylethylamino)-6-methyl-2-oxo-2H-pyrazin-1-yl]-acetic acid and 2,2-difluoro-2-(2-pyridyl)ethyl amine essentially according to the procedure of Example 1, Step K. Mass Spectrum: Found: (M+1) 465.2.

EXAMPLE 7

Preparation of N-(2,2-Difluoro-2-pyridin-4-yl-ethyl)-2-[3-(2,2-difluoro-2-pyridin-2-yl-ethylamino)-6-methyl-2-oxo-2H-pyrazin-1-yl]-acetamide

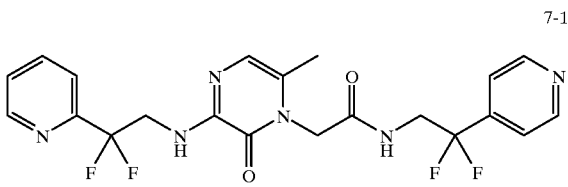

7-1 was prepared from [3-(2,2-difluoro-2-pyridin-2-yl-ethylamino)-6-methyl-2-oxo-2H-pyrazin-1-yl]-acetic acid and 2,2-difluoro-2-(4-pyridyl)ethyl amine essentially according to the procedure of Example 1, Step K. Mass Spectrum: Found: (M+1) 465.2.

EXAMPLE 8

Preparation of 2-[3-(2,2-Difluoro-2-pyridin-2-yl-ethylamino)-6-methyl-2-oxo-2H-pyrazin-1-yl]-N-phenethyl-acetamide

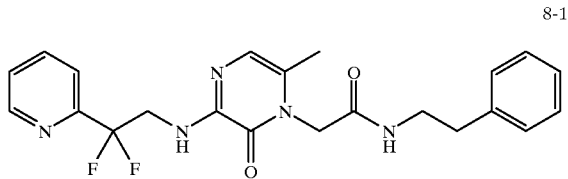

8-1 was prepared from [3-(2,2-difluoro-2-pyridin-2-ylethylamino)-6-methyl-2-oxo-2H-pyrazin-1-yl]-acetic acid and phenethylamine essentially according to the procedure of Example 1, Step K. Mass Spectrum: Found: (M+1) 428.2.

EXAMPLE 9

Preparation of 2-[6-Chloro-3-(2,2-difluoro-2-pyridin-2-yl-ethylamino)-2-oxo-2H-pyrazin-1-yl]-N-(2,2-difluoro-2-pyridin-2-yl-ethyl)-acetamide

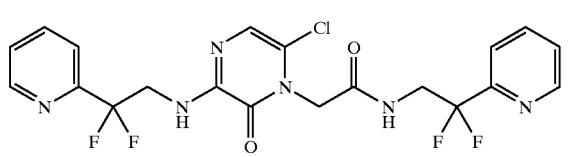

Step A: Ethyl N-(ethyl carboxymethyl)oxamate (9-1)

To a suspension of ethyl glycine·HCl (38.4 g, 275 mmol) in 1,2-dichloroethane (360 ml) was added triethylamine (77.0 mL, 550 mmol) at room temperature. After stirring for 30 minutes the heterogenous mixture was cooled to 0° C. and ethyl oxalyl chloride (30.3 ml, 275 mol) was added dropwise over the course of 1 h. Upon completion of the addition, the cooling bath was removed and the reaction was stirred at room temperature overnight. The reaction was diluted with water (250 ml) and the layers separated. The aqueous layer was extracted with 2 portions of dichloromethane (250 ml). The combined organic layers were washed with water (250 ml), followed by brine (250 ml), dried over MgSO$_4$ and concentrated to give an oil 9-1 that was taken directly onto the next step.

Step B: N-(Ethyl carboxymethyl)-N'-(2,2-dimethoxyethyl) oxamide (9-2)

To a solution of the oxamate 9-1 (84.0 g, 414 mmol) in 2-propanol (500 ml) was added aminoacetaldehyde dimethyl acetal (45.7 g, 435 mmol) in one portion. After stirring overnight at room temperature, the reaction mixture was concentrated to a thick orange oil. This thick slurry was diluted with 2-propanol (300 ml) and the solid was broken up with a spatula. Filtration afforded a solid which was further rinsed with an additional portion of 2-propanol. Removal of residual 2-propanol was accomplished via high vacuum to afford a light orange solid 9-2: $^1$H NMR (CDCl$_3$) δ7.82 (br s, 1H), 7.50 (br s, 1H), 4.41 (t, 1H, 5.3 Hz), 4.24 (q, 2H, 7.1 Hz), 4.09 (d, 2H, 5.9 Hz), 3.47 (dd, 2H, 5.3, 6.2 Hz), 3.40 (s, 6H), 1.30 (t, 3 H, 7.1 Hz).

Step C: Ethyl 3-hydroxypyrazin(1H)-2-one-1-acetate (9-3)

A solution of the oxamide 9-2 (89.8 g, 343 mmol), acetic acid (400 ml), and conc. HCl (2 ml) was heated to reflux. After 1 h the black reaction was concentrated to a thick oil (high vacuum employed to ensure complete removal of AcOH) which was diluted with EtOH (150 ml) and MeOH (150 ml). Scraping the thick black oil with a spatula induced precipitation of the product. The MeOH was removed via rotary evaporation and the remaining slurry was filtered and rinsed with EtOH (200 ml) to deliver a tan solid. Recrystallization from refluxing EtOH (300 ml) afforded an off-white powder 9-3: $^1$H NMR (CD$_3$OD) δ6.50 (d, 1H, 5.9 Hz), 6.36 (d, 1H, 5.9 Hz), 4.58 (s, 2H), 4.23 (q, 2H, 7.1 Hz), 1.28 (t, 3 H, 7.1 Hz). Further crude dione could be obtained upon concentration of the mother liquor.

Step D: Ethyl 3-bromopyrazin(1H)-2-one-1-acetate (9-4)

A solution of the hydroxypyrazinone 9-3 (25.0 g, 126 mmol) and phosphorous oxybromide (37.9 g, 132 mmol) in 1,2-dichloroethane (250 ml) was heated to reflux. After 8 h the reaction mixture was treated with sat. aq. Na$_2$CO$_3$ (250 ml) and stirred for 1 h. The mixture was diluted with water (100 ml) and dichloromethane (100 ml), the layers were separated and the aqueous layer was extracted with EtOAc (3×200ml). The combined organics were dried (MgSO4), and concentrated to give an oil which was stored under high vacuum overnight to afford brown solid 9-4: $^1$H NMR (CDCl$_3$) δ7.17 (d, 1H, 4.2 Hz), 7.07 (d, 1H, 4.2 Hz), 4.65 (s, 2H), 4.27 (q, 2H, 7.2 Hz), 1.31 (t, 3 H, 7.2 Hz).

Step E: Ethyl 3-(2,2-difluoro-2-(2-pyridylethylamino) pyrazin(1H)-2-one-1-acetate (9-5)

A solution of 4.80 g (30.4 mmol) of 2,2-difluoro-2-(2-pyridyl)ethylamine, 4.24 mL (30.4 mmol) of triethylamine and 7.93 g (30.4 mmol) of ethyl 3-bromopyrazin(1H)-2-one-1-acetate 9-4 was heated to 120° C. in a sealed tube overnight in 12 ml of toluene and 4 ml of ethanol. The reaction was concentrated and the residue was partitioned between dichloromethane and sat. aq. NaHCO$_3$. The aqueous layer was extracted with 4 portions of dichloromethane. The combined organic layers were dried over MgSO$_4$ and the solvents removed under reduced pressure to give an oil that was chromatographed on using 3:2 to 2:3 hexane/EtOAc to give a yellow solid 9-5: $^1$H NMR (CDCl$_3$) δ8.67 (dd, 1H, 4.8, 0.7 Hz), 7.81 (ddd,1H, 7.8, 7.8, 1.7 Hz), 7.69 (dd, 1H, 7.8, 1 Hz), 7.38 (dd, 1H, 5.1, 7.0 Hz), 6.86 (d, 1H, 4.8 Hz), 6.54 (br t, 1H, 5.9 Hz), 6.40 (d, 1H, 4.6 Hz), 4.54 (s, 2H), 4.38 (td, 2H, 14.0, 6.4 Hz), 4.24 (q, 2H, 7.1 Hz), 1.29 (t, 3 H, 7.1 Hz).

Step F: Ethyl 3-(2,2-difluoro-2-(2-pyridylethylamino)-6-chloro-pyrazin(1H)-2-one-1-acetate (9-6)

To a stirred solution of 6.81 g (20.1 mmol) of ethyl 3-(2,2-difluoro-2-(2-pyridylethylamino)pyrazin(1H)-2-one-1-acetate 10-5 and 2.42 g (18.1 mmol) of N-chlorosuccinimide in 100 ml of 1,2-dichloroethane was heated to reflux. An additional 242 mg (1.81 mmol) and 75 mg (0.56 mmol) of NCS were added to the reaction mixture after 1 h and 1.5 h, respectively. After 2.5 h total, the solution was cooled to room temperature and partitioned between dichloromethane (150 ml) and sat. aq. NaHCO$_3$ (200 ml). The layers were separated and the aqueous phase was extracted with dichloromethane (2×200 ml). The combined organic layers were dried over MgSO$_4$ and the solution concentrated to a volume of 10 ml. This liquid was directly loaded onto a SiO$_2$ column and eluted with 65:35 to 55:45 hexane/EtOAc to give a yellow solid 9-6: $^1$H NMR (CDCl$_3$) δ8.68 (d, 1H, 4.8, Hz), 7.83 (ddd,1H, 7.7, 7.7, 1.6 Hz), 7.9 (dd, 1H, 7.9 Hz), 7.40 (dd, 1H, 4.9, 7.3 Hz), 6.96 (s, 1H), 6.49 (br t, 1H, 5.9 Hz), 4.89 (s, 2H), 4.38 (td, 2H, 13.9, 6.5 Hz), 4.26 (q, 2H 7.1 Hz), 1.30 (t, 3 H, 7.1 Hz).

Step G: 3-(2,2-Difluoro-2-(2-pyridylethylamino)-6-chloropyrazin(1H)-2-one-1-acetic acid (9-7)

To a stirred solution of 7.27 g (19.5 mmol) of ethyl 3-(2,2-difluoro-2-(2-pyridylethylamino)-6-chloropyrazin (1H)-2-one-1-acetate 9-6 in 200 ml of methanol was added 39 ml (39.0 mmol) of 1M aq. potassium hydroxide. After 3 h the solution was acidified to pH=7 using conc. HCl, and concentrated at reduced pressure (azeotrope with PhCH$_3$) to give a white solid containing potassium chloride and 9-7: $^1$H NMR (CD$_3$OD) δ8.64 (d, 1H, 4.8 Hz), 7.93 (ddd,1H, 7.7, 7.7, 1.5 Hz), 7.70 (d, 1H, 8.0 Hz), 7.49 (dd, 1H, 5.2, 7.4 Hz), 6.80 (s, 1H), 4.67 (s, 2H), 4.27 (t,2H, 13.9 Hz).

Step H: 2-[6-Chloro-3-(2,2-difluoro-2-pyridin-2-yl-ethylamino)-2-oxo-2H-pyrazin-1-yl]-N-(2,2-difluoro-2-pyridin-2-yl-ethyl)-acetamide (9-8)

9-8 was prepared from 3-(2,2-difluoro-2-(2-pyridylethylamino)-6-chloropyrazin(1H)-2-one-1-acetic acid and 2,2-difluoro-2-(2-pyridyl)ethylamine 9-7 essentially according to the procedure of Example 1, Step K.: $^1$H NMR (CD$_3$OD) δ8.77 (d, 2H, 5.1 Hz), 8.24 (m, 2H), 7.95 (m, 2H), 7.77 (m, 2H), 6.86 (s, 1H), 2H), 4.40 (t, 2H, 13.9 Hz), 4.14 (t, 2H, 13.9 Hz). Mass Spectrum: Found: (M+1) 485.1

Typical tablet cores suitable for administration of thrombin inhibitors are comprised of, but not limited to, the following amounts of standard ingredients:

| Excipient | General Range (%) | Preferred Range (%) | Most Preferred Range (%) |
|---|---|---|---|
| Suggested Ranges of Composition for Excipients in Uncoated Tablet Cores | | | |
| mannitol | 10–90 | 25–75 | 30–60 |
| microcrystalline cellulose | 10–90 | 25–75 | 30–60 |
| magnesium stearate | 0.1–5.0 | 0.1–2.5 | 0.5–1.5 |

Mannitol, microcrystalline cellulose and magnesium stearate may be substituted with alternative pharmaceutically acceptable excipients.

IN VITRO ASSAY FOR DETERMINING PROTEINASE INHIBITION

Assays of human α-thrombin and human trypsin were performed by the methods substantially as described in *Thrombosis Research*, Issue No. 70, page 173 (1993) by S. D. Lewis et al.

The assays were carried out at 25° C. in 0.05 M TRIS buffer pH 7.4, 0.15 M NaCl, 0.1% PEG. Trypsin assays also contained 1 mM CaCl$_2$. In assays wherein rates of hydrolysis of a p-nitroanilide (pna) substrate were determined, a Thermomax 96-well plate reader was used was used to measure (at 405 nm) the time dependent appearance of p-nitroaniline. sar-PR-pna was used to assay human αthrombin (K$_m$=125 μM) and bovine trypsin (K$_m$=125 μM). p-Nitroanilide substrate concentration was determined from measurements of absorbance at 342 nm using an extinction coefficient of 8270 cm$^{-1}$M$^{-1}$.

In certain studies with potent inhibitors (K$_i$<10 nM) where the degree of inhibition of thrombin was high, a more sensitive activity assay was employed. In this assay the rate of thrombin catalyzed hydrolysis of the fluorogenic substrate Z-GPR-afc (K$_m$=27 μM) was determined from the increase in fluorescence at 500 nm (excitation at 400 nm) associated with production of 7-amino-4-trifluoromethyl coumarin. Concentrations of stock solutions of Z-GPR-afc were determined from measurements of absorbance at 380 nm of the 7-amino-4-trifluoromethyl coumarin produced upon complete hydrolysis of an aliquot of the stock solution by thrombin.

Activity assays were performed by diluting a stock solution of substrate at least tenfold to a final concentration <0.1 K$_m$ into a solution containing enzyme or enzyme equilibrated with inhibitor. Times required to achieve equilibration between enzyme and inhibitor were determined in control experiments. Initial velocities of product formation in the absence (V$_o$) or presence of inhibitor (V$_i$) were measured. Assuming competitive inhibition, and that unity is negligible compared K$_m$/[S], [I]/e, and [I]/e (where [S], [I], and e respectively represent the total concentrations, of substrate, inhibitor and enzyme), the equilibrium constant (K$_i$) for dissociation of the inhibitor from the enzyme can be obtained from the dependence of V$_o$/V$_i$ on [I] shown in equation 1.

$$V_o/V_i = 1 + [I]/K_i \quad (1)$$

The activities shown by this assay indicate that the compounds of the invention are therapeutically useful for treating various conditions in patients suffering from unstable angina, refractory angina, myocardial infarction, transient ischemic attacks, atrial fibrillation, thrombotic stroke, embolic stroke, deep vein thrombosis, disseminated intravascular coagulation, and reocclusion or restenosis of recanalized vessels. The inhibitory activity of compounds of the invention against human thrombin, represented by Ki, is less than 24 nM. These are selective compounds, as evidenced by their inhibitory activity against human trypsin (represented by Ki), which is at least 1000 nM.

EXAMPLE 10

Tablet Preparation

Tablets containing 25.0, 50.0, and 100.0 mg., respectively, of the following active compounds are prepared as illustrated below (compositions A-I), Active I is N-(2,2-Difluoro-2-pyridin-4-yl-ethyl)-2-{3-(2,2-difluoro-2-pyridin-2-yl-ethylamino)-6-methyl-2-oxo-2H-pyrazin-1-yl }-acetamide; Active II is 2-[6-Chloro-3-(2,2-diflouro-2-pyridin-2-yl-ethylamino)-2-oxo-2H-pyrazin-1-yl]-N-[2,2-diflouro-2-pyridin-2-yl-ethyl)-acetamide; Active III is N-(2, 2-Difluoro-2-pyridin-2-ylethyl)-2-[6-methyl-2-oxo-3-(2-pyridin-2-yl)amino-2H-pyrazin-1-yl]acetamide.

TABLE FOR DOSES CONTAINING FROM
25–100 MG OF THE ACTIVE COMPOUND

| Component | Amount-mg | | | | | | | | |
|---|---|---|---|---|---|---|---|---|---|
| | A | B | C | D | E | F | G | H | I |
| Active I | 25 | 50 | 100 | — | — | — | — | — | — |
| Active II | — | — | — | 25 | 50 | 100 | — | — | — |
| Active III | — | — | — | — | — | — | 25 | 50 | 100 |
| Microcrystalline Cellulose | 37.25 | 100 | 200 | 37.25 | 100 | 200 | 37.25 | 100 | 200 |
| Modified food corn starch | 37.25 | 4.25 | 8.5 | 37.25 | 4.25 | 8.5 | 37.25 | 4.25 | 8.5 |
| Magnesium stearate | 0.5 | 0.75 | 1.5 | 0.5 | 0.75 | 1.5 | 0.5 | 0.75 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 25.0, 50.0, and 100.0 mg, respectively, of active ingredient per tablet.

EXAMPLE 11

Tablet Preparation

Exemplary compositions of 2-[3-(2,2-Difluoro-2-pyridin-2-yl-ethylamino)-6-methyl-2-oxo-2H-pyrazin-1-yl]-N-(2-pyridin-3-ylethyl)-acetamide (Active IV) tablets are shown below:

| Component | 0.25 mg | 2 mg | 10 mg | 50 mg |
|---|---|---|---|---|
| Active IV | 0.500% | 1.000% | 5.000% | 14.29% |
| mannitol | 49.50% | 49.25% | 47.25% | 42.61% |
| microcrystalline cellulose | 49.50% | 49.25% | 47.25% | 42.61% |
| magnesium stearate | 0.500% | 0.500% | 0.500% | 0.500% |

2, 10 and 50 mg tablets were film-coated with an aqueous dispersion of hydroxypropyl cellulose, hydroxypropyl methylcellulose and titanium dioxide, providing a nominal weight gain of 2.4%.

Tablet Preparation Via Direct Compression

Active IV, mannitol and microcrystalline cellulose were sieved through mesh screens of specified size (generally 250 to 750 μm) and combined in a suitable blender. The mixture was subsequently blended (typically 15 to 30 min) until the drug was uniformly distributed in the resulting dry powder blend. Magnesium stearate was screened and added to the blender, after which a precompression tablet blend was achieved upon additional mixing (typically 2 to 10 min). The precompression tablet blend was then compacted under an applied force, typically ranging from 0.5 to 2.5 metric tons, sufficient to yield tablets of suitable physical strength with acceptable disintegration times (specifications will vary with the size and potency of the compressed tablet). In the case of the 2, 10 and 50 mg potencies, the tablets were dedusted and film-coated with an aqueous dispersion of water-soluble polymers and pigment.

Tablet Preparation Via Dry Granulation

Alternatively, a dry powder blend is compacted under modest forces and remilled to afford granules of specified particle size. The granules are then mixed with magnesium stearate and tabletted as stated above.

EXAMPLE 12

Intravenous Formulations

Intravenous formulations of 2-[3-(2,2-Difluoro-2-pyridin-2-yl-ethylamino)-6-methyl-2-oxo-2H-pyrazin-1-yl]-N-(2-pyridin-3-ylethyl)-acetamide (Active IV) were prepared according to general intravenous formulation procedures.

| Component | Estimated range |
|---|---|
| Active IV | 0.12–0.61 mg |
| D-glucuronic acid* | 0.5–5 mg |
| Mannitol NF | 50–53 mg |
| 1N Sodium Hydroxide | q.s. pH 3.9–4.1 |
| Water for injection | q.s. 1.0 mL |

Exemplary compositions A-C are as follows:

| Component | A | B | C |
|---|---|---|---|
| Active IV | 0.61 mg* | 0.30** | 0.15*** |
| D-glucuronic acid* | 1.94 mg | 1.94 mg | 1.94 mg |
| Mannitol NF | 51.2 mg | 51.2 mg | 51.2 mg |
| 1N Sodium Hydroxide | q.s. pH 4.0 | q.s. pH 4.0 | q.s. pH 4.0 |
| Water for injection | q.s. 1.0 mL | q.s. 1.0 mL | q.s. 1.0 mL |

*0.50 mg free base
**0.25 mg free base
***0.12 mg free base

Various other buffer acids, such as L-lactic acid, acetic acid, citric acid or any pharmaceutically acceptable acid/conjugate base with reasonable buffering capacity in the pH range acceptable for intravenous administration may be substituted for glucuronic acid.

What is claimed is:

1. A compound having the formula:

[Chemical structure of the general formula with W, R², X, V, R¹ substituents on a pyrazinone core]

wherein
W is

[Pyridine structures with R³ substituent, 2- or 4-position] or ;

V is

[Pyridine structures, 2- or 4-position], , or

[Phenyl with R₄ substituent];

X is halogen, C$_{1-4}$alkyl, or cyano;

R$^1$ is hydrogen or halogen, provided that when R$^2$ is hydrogen, R$^1$ is halogen;

R$^2$ is hydrogen or halogen, provided that when R$^1$ is hydrogen, R$^2$ is halogen;

R$^3$ is hydrogen or C$_{1-4}$alkyl; and

R$^4$ is hydrogen, halogen, or C$_{1-4}$ alkyl, or a pharmaceutically acceptable salt thereof.

2. A compound of claim 1, or a pharmaceutically acceptable salt thereof, wherein X is Cl or CH$_3$.

3. A compound of claim 2, or a pharmaceutically acceptable salt thereof, wherein R$^1$ is hydrogen or F.

4. A compound of claim 3, or a pharmaceutically acceptable salt thereof, wherein R$^2$ is hydrogen or F.

5. A compound of claim 4, or a pharmaceutically acceptable salt thereof, wherein R$^3$ is hydrogen or CH$_3$, and R$^4$ is hydrogen or Cl.

6. The compound of claim 5, or a pharmaceutically acceptable salt thereof, selected from the group consisting of:

[Chemical structures of specific compounds]

7. A composition comprising a compound of claim 1 and a pharmaceutically acceptable carrier.

8. A method for inhibiting thrombin in blood comprising adding to the blood a composition of claim 7.

9. A method for inhibiting thrombus formation in blood comprising adding to the blood a composition of claim 7.

10. A method for treating or preventing venous thromboembolism and pulmonary embolism in a mammal comprising administering to the mammal a composition of claim 7.

11. A method for treating or preventing deep vein thrombosis in a mammal comprising administering to the mammal a composition of claim 7.

12. A method for treating or preventing thromboembolic stroke in humans and other mammals comprising administering to the mammal a composition of claim 7.

13. A method for treating or preventing atherosclerosis in a mammal comprising administering to the mammal a composition of claim 7.

14. A method for treating or preventing thrombosis in a mammal with inherited thrombophilic diseases such as Protein C deficiency, Protein S deficiency, antithrombin III and factor V Leiden comprising administering to the mammal a composition of claim 7.

15. A method for treating or preventing thrombosis in a mammal with acquired thrombophilic disorders such as systemic lupus erythematosus comprising administering to the mammal a composition of claim 7.

16. A method for lowering the propensity of a device which contacts blood to clot blood which comprises coating the device with a composition of claim 7.

17. A method for treating or preventing reocclusion in a mammal during or following percutaneous transluminal coronary angioplasty comprising administering to the mammal a composition of claim 7.

18. A method for treating or preventing occlusive cerebrovascular disease in a mammal comprising administering to the mammal a composition of claim 7.

19. A method for maintaining patency in arteriovenous cannulas inserted in a mammal comprising administering to the mammal a composition of claim 7.

* * * * *